(12) United States Patent
Hoskuldsson et al.

(10) Patent No.: US 9,192,316 B2
(45) Date of Patent: Nov. 24, 2015

(54) SYSTEMS AND METHODS USING FLEXIBLE CAPACITIVE ELECTRODES FOR MEASURING BIOSIGNALS

(75) Inventors: Sveinbjorn Hoskuldsson, Reykjavik (IS); Bjorgvin Gudmundsson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 887 days.

(21) Appl. No.: 13/320,564

(22) PCT Filed: May 17, 2010

(86) PCT No.: PCT/IS2010/000007
§ 371 (c)(1),
(2), (4) Date: Jan. 10, 2012

(87) PCT Pub. No.: WO2010/131267
PCT Pub. Date: Nov. 18, 2010

(65) Prior Publication Data
US 2012/0101357 A1    Apr. 26, 2012

(30) Foreign Application Priority Data
May 15, 2009  (DK) ................................. 2009 00624

(51) Int. Cl.
*A61B 5/0428*    (2006.01)
*A61B 5/08*      (2006.01)
(Continued)

(52) U.S. Cl.
CPC ............. *A61B 5/0408* (2013.01); *A61B 5/0478* (2013.01); *A61B 5/04085* (2013.01);
(Continued)

(58) Field of Classification Search
CPC .............. A61B 5/1135; A61B 5/0408; A61B 5/04085; A61B 5/04284; A61B 5/0479; A61B 5/0492; A61B 5/0809; A61B 5/4806; A61B 5/6804; A61B 5/6805; A61B 5/6831
USPC .................. 600/386, 529, 534–536, 547, 388
See application file for complete search history.

(56) References Cited

U.S. PATENT DOCUMENTS 3,347,223 A    10/1967  Pacela
3,500,823 A     3/1970  Richardson
(Continued)

FOREIGN PATENT DOCUMENTS

DE    199 41 500 A1    3/2001
WO       02/02013 A1    1/2002
(Continued)

OTHER PUBLICATIONS

International Search Report PCT/IS2010/000007; Dated Oct. 1, 2010.
(Continued)

*Primary Examiner* — Lee S Cohen
*Assistant Examiner* — Erin M Cardinal
(74) *Attorney, Agent, or Firm* — Workman Nydegger

(57) ABSTRACT

A system is provided for measuring biometric signals, including at least two electrodes, wherein at least one is a capacitive electrode with a flexible structure, the system having a circuit for measuring the voltage between the two electrodes, where in some embodiments both electrodes are capacitive electrodes, and can be arranged as flexible belts, the system being suitable for measuring ECG signals and can be configured to measure also respiratory effort with Respiratory Inductive Plethysmography (RIP) technology, using the same electrodes which are used for measuring capacitively the ECG signals, a method being further provided for measuring biosignals with the system of the invention, the method further including generating an added current signal with a signal generator connected to the circuit, where the added signal has a frequency substantially removed from the frequency of the biosignal of interest, and by measuring the voltage signal of the frequency component corresponding to the added current signal one can determine fluctuations in the overall impedance and fluctuations in the capacitance of the circuit, and correct for fluctuations in the capacitance to obtain a corrected voltage signal representing the measured biosignal.

19 Claims, 3 Drawing Sheets

(51) Int. Cl.
  *A61B 5/0408* (2006.01)
  *A61B 5/0478* (2006.01)
  *A61B 5/0492* (2006.01)
  *A61B 5/113* (2006.01)
  *A61B 5/00* (2006.01)

(52) U.S. Cl.
  CPC .......... *A61B5/0492* (2013.01); *A61B 5/04284* (2013.01); *A61B 5/0809* (2013.01); *A61B 5/1135* (2013.01); *A61B 5/6804* (2013.01); *A61B 5/6805* (2013.01); *A61B 5/6831* (2013.01); *A61B 5/4806* (2013.01); *A61B 5/721* (2013.01)

(56) References Cited

U.S. PATENT DOCUMENTS

| | | | |
|---|---|---|---|
| 4,373,534 | A | 2/1983 | Watson |
| 5,331,968 | A * | 7/1994 | Williams et al. ............. 600/534 |
| 5,348,008 | A * | 9/1994 | Bornn et al. ................ 600/301 |
| 5,353,793 | A * | 10/1994 | Bornn .......................... 600/386 |
| 6,148,486 | A | 11/2000 | Uehara et al. |
| 6,327,486 | B1 * | 12/2001 | Nissila et al. ................. 600/372 |
| 6,341,504 | B1 * | 1/2002 | Istook ......................... 66/172 E |
| 6,461,307 | B1 * | 10/2002 | Kristbjarnarson et al. ... 600/534 |
| 6,807,438 | B1 * | 10/2004 | Brun Del Re et al. ........ 600/372 |
| 7,593,767 | B1 | 9/2009 | Modarres |
| 8,193,821 | B2 | 6/2012 | Mueller et al. |
| 2002/0032386 | A1 * | 3/2002 | Sackner et al. .............. 600/536 |
| 2002/0032388 | A1 | 3/2002 | Kristbjarnarson et al. |
| 2003/0135127 | A1 | 7/2003 | Sackner |
| 2005/0054941 | A1 | 3/2005 | Ting |
| 2005/0119586 | A1 | 6/2005 | Coyle et al. |
| 2006/0122528 | A1 * | 6/2006 | Gal ............................... 600/534 |
| 2006/0282001 | A1 * | 12/2006 | Noel et al. .................... 600/535 |
| 2007/0167089 | A1 | 7/2007 | Gobron et al. |
| 2009/0259135 | A1 * | 10/2009 | Stasz ............................ 600/534 |
| 2010/0060300 | A1 | 3/2010 | Muller et al. |
| 2010/0297868 | A1 | 11/2010 | Hermannsson |
| 2011/0248729 | A2 | 10/2011 | Mueler et al. |

FOREIGN PATENT DOCUMENTS

| | | |
|---|---|---|
| WO | 02/080761 A2 | 10/2002 |
| WO | 2006066566 A2 | 6/2006 |

OTHER PUBLICATIONS

Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.

Stromberg, N.O.T., "Error analysis of a natural breathing calibration method for respiratory inductive plethysmography", Medical & Biological Engineering & Computing 2001, vol. 39, No. 3, May 1, 2001, pp. 310-314.

Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.

International Search Report from Corresponding PCT Application No. PCT/IB2014/002760, Mar. 27, 2015.

* cited by examiner

SYSTEMS AND METHODS USING FLEXIBLE CAPACITIVE ELECTRODES FOR MEASURING BIOSIGNALS

FIELD OF THE DISCLOSURE

The present disclosure relates to the field biometric systems for electronic measurements of biosignals, including electrocardiography signals and breathing measurements.

TECHNICAL BACKGROUND

Electrophysiological signals from human or animal bodies are some of the most fundamental signals used in medical diagnostics. Such signals originate from the muscular, cardiac or neurological electronic activity of a living body.

For recording of heart, muscular or neurological electric activities (including the methods of Electrocardiography (ECG), Electromyography (EMG), Electroencephalography (EEG) and Electrooculography (EOG)) skin-electrodes are normally glued to the skin of the patient. The measured signal is based on the potential between the electrodes, which is dependent on the sum of the neural and muscular electronic activity between the electrodes. The quality of the signal is greatly affected by the accuracy of the position of the electrode and the conductance of the skin. For this reason the surface-skin must be scrubbed off and various fluids or gels are used, to get the electrode in direct galvanic contact with the internal body fluids. This makes the use of electrodes semi-invasive and makes it difficult for other than health-professionals to perform the setup. This can often be a problem, e.g. for sleep research and diagnosis, where overnight measurements are needed.

Sleep Studies

To get accurate results from a sleep study, the patient must feel comfortable and sleep normally. Studies have shown that there is a significant difference between the results from the first night measured and the following nights, when the patient is more comfortable with the studies. Optimally the patient should therefore be measured for two or more nights.

When a full sleep diagnostic study (polysomnography, PSG) is performed, a combination of parameters are measured, including the above mentioned electrophysiological parameters along with large number of other sensor signals. The complication of the setup is therefore high and the setup is fragile and uncomfortable for the patient. The result is that this kind of study is mostly done at a hospital or specialized sleep clinics and for one night only. PSG ambulatory sleep studies performed at people's homes are less common due to these complications; even with the obvious benefits of measuring the patient in his conventional environment and resulting reduction of cost.

Electrocardiography (ECG) is an important tool for sleep diagnostics and gives valuable indicators due to its connection with sleep-related parameters, blood pressure and arousals. Heart-rate-variability (HRV) and pulse-transit-time (PTT) are examples of useful parameters that provide significant indications on the sleep/wake pattern of a subject.

If setup of more complicated sensors, like ECG electrodes, could be performed by a patient or assistant at home, this would increase the quality of the studies, save work and make multiple-night sleep recordings possible.

Capacitive Electrodes

The general idea of capacitive electrodes is to use a different way of measuring up the electrophysiological signals, such as for example ECG signals. When using conventional electrodes, the aim is to provide a good signal connection by minimizing the electronic resistance between the electrode lead and the patient body fluids. The idea behind electrocapacitive electrodes is however instead of basing the signal conductivity on resistance, to form a maximum capacitance connection for the same purpose. As the conductivity of capacitance is variable with frequency this does however require that the amplifier input resistance must be extremely high, for the signal in the band-width of interest to be detected.

The simplest form of a capacitor between the body and the electrode lead would be a metallic plate, where the surface has been coated with a thin layer of isolating material. By pressing the plate towards the body a parallel plate capacitor has been formed. Any electronic activity in the body will cause electronic field to be formed over the isolating material of the plate. By measuring the field or the voltage caused by the field, the electronic body signals can be measured the same way as when conventional electrodes are being used, but without being in direct galvanic contact with the body.

Such capacitive electrode can be generally described by equation (1):

$$C = \epsilon * A/d \qquad (1)$$

where $\epsilon$ is a constant, A is the area of the surface of the electrode, d is the effective insulating distance (the distance between the electrode surface and the bodily fluids constituting the inherent "circuit" of the body).

This kind of electrode was first described in the late 60s and patented in 1970. (P. Richardson and A. Lopez, Jr., "Electrocardiographic and Bioelectric Capacitive Electrode," U.S. Pat. No. 3,500,823, granted 17 Mar. 1970). The capacitive electrode disclosed by Richardson and Lopez comprises a round disk, 1.5 in diameter, and 0.125 in thick, with an insulating coating on the surface facing the skin of a subject. Typical characteristics of such electrode include a resistance of greater than 4 GΩ (Gigaohms) at 50 V and a capacitance of 5000 pF (picofarad) at 30 Hz.

The general problems of such capacitive electrode include that the signal amplifier used must have an impedance value on par with the high impedance of the electrode and preferably substantially higher, so as not to lose too much of the signal potential, before the signal is measured. A second more complicated problem is that the impedance of the electrode is variable, depending on the distance 'd', between the electrode surface and the bodily fluids, which distance will change as a result of bodily movements (e.g. breathing). This second problem has been generally addressed by having a very thin insulating layer on the electrode to increase the capacitance, and by strapping the electrode rigidly to the body so as to minimize the fluctuations in the distance d and thus fluctuations in C.

SUMMARY

The present disclosure provides in a first aspect a system for measuring biometric signals, the system comprising at least two electrodes wherein at least one of which is a flexible capacitive electrode. Preferably, the second electrode is as well a capacitive electrode having a flexible structure. The system can suitably comprise at least two flexible conducting electrodes that can be placed on or around the body of a subject, wherein voltage is measured between the two electrodes.

The present disclosure utilises new circuit design and measurement configuration, such that the measured capacitive signal can provide a well resolved and accurate measurement of biosignals, e.g. ECG measurements, decoupling the effects of the high variability of the capacitance of the circuit.

The at least two electrodes may suitably be arranged as flexible belts, preferably these are elastically deformable, such that they can be fit snugly on the torso of a subject.

In one embodiment, the system comprises two electrodes configured to be placed around the thorax and abdomen respectively, of a subject. In such embodiment, the system can suitably be configured to simultaneously determine the respiratory effort of the patient. Preferably, in such system the electrodes form flexible belts for determining respiratory effort based on Respiratory Inductive Plethysmography (RIP) technology.

It follows that the electrodes as described herein can in one embodiment form at least two belts for determining respiratory effort as a simultaneous measurement with a capacitance measurement for determining electrocardiography (ECG) signals. Preferably the electrodes form belts for determining respiratory effort based on Respiratory Inductive Plethysmography (RIP) technology, but other means for measuring respiratory effort are as well encompassed by the concepts of the present disclosure, as described in more detail herein.

Another aspect of the present disclosure provides a method for measuring biosignals from a subject, comprising:
  placing at least one flexible capacitive electrode on the subject, connected in a circuit,
  measuring the voltage between said at least one flexible capacitive electrode and a reference point and transmitting a signal to a high-input impedance amplifier, and
  processing the received signal and outputting a useful biosignal.

The method can suitably be performed with a system such as described herein.

In a preferred embodiment the method further comprises
  generating an added current signal with a signal generator connected to said circuit, said added signal having a frequency substantially removed from the frequency of the biosignal of interest,
  measuring the voltage signal of the frequency component corresponding to the added current signal to thereby determine fluctuations in the overall impedance and fluctuations in the capacitance of the circuit, and
  correct for fluctuations in the capacitance to obtain a corrected voltage signal representing the measured biosignal and outputting said signal.

DETAILED DESCRIPTION

Figure 1:
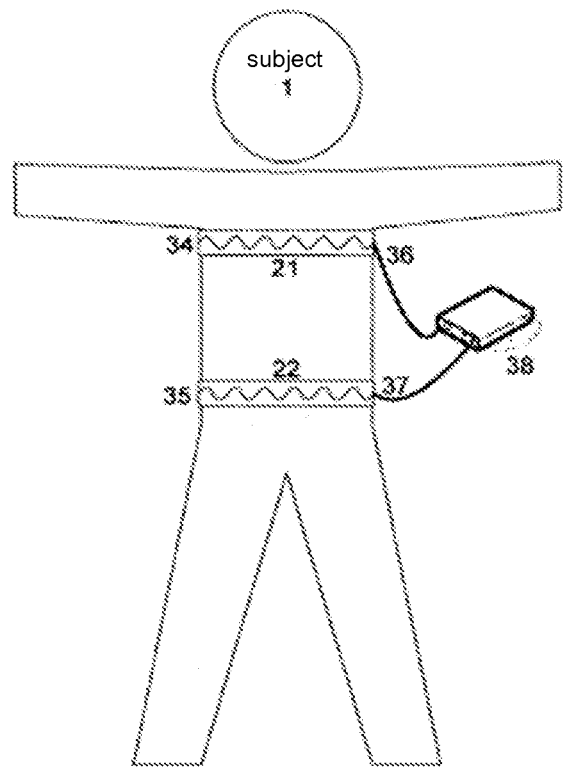
FIG. 1 illustrates a system of the present disclosure according to a first embodiment with electrodes in the form of conductive belts wrapped around the thorax 34 and abdomen 35 of a person 1.

Prior art electrodes for formation of capacitive electrodes do have in common that they are based on a rigid plate that is pressed toward some place of the body where the desired signal is located.

The use of flexible and/or elastic electrodes as in the present disclosure provide critical benefits, and certain challenges as well, which however are solved by the present disclosure.

The present disclosure provides a different concept of using capacitive electrodes for measuring biosignals. The present disclosure is based on using a flexible electrode, such as in particular a belt, a cord, a sheet or the like. The term "flexible" as used in this context indicates an electrode with a structure which can have substantially varying capacitance during use, i.e. the capacitor formed between the electrode and the body of a subject may and generally will vary when in use on a live subject, and no particular measures need be taken to eliminate or minimize such variations, as in prior art systems based on rigid capacitive electrodes.

Preferably, the electrode is flexibly adjustable such that it can be fit snugly on a subject, but without having to restrict normal movements of the subject. Thus, systems and electrodes of the present disclosure can be used for sleep measurements where the subject can rest and sleep comfortably, while the electrodes are mounted and the system in operation.

In certain embodiments, the capacitive electrodes can be formed by one or more of the following:
  Weaving, sewing or knitting of conductive material into flexible and/or elastic material,
  Lamination of conductive material between layers of flexible and/or elastic material,
  Gluing of conductive material onto the surface of flexible and/or elastic material,
  Coating a flexible and/or elastic material with conductive film The belts electrodes can in some embodiments be described by the term "textile-like", which in this context is meant to describe any type of fabric, including woven, sewn or knitted fabric but the electrodes may also be of plastic type or from rubber or a rubber-like material, or any mixtures or combination of the above.

The present disclosure encompasses systems with at least one flexible capacitive electrode, and a reference point, which can be a conventional electrode mounted on the subject but is in preferred embodiments described herein a second capacitive electrode.

It is however within the scope of the present disclosure to use alternative electrode setup, based on the same principles described herein. For example, a setup with one electrode mounted on the front of the torso of a subject and an opposite electrode on the back of the subject, can as well be used for capacitive measurements as described herein.

As mentioned above, one of the great challenges when using flexible electrodes is that movements of the electrodes result in capacitance changes that directly affect the measured signal and this results in disturbances and errors. The voltage over a capacitor is inversely modulated by the change in capacitance. It is very difficult to keep the capacitance constant of the capacitor formed between a capacitive electrode and the body, as movements do cause disturbances to occur that can be deleterious to the measurement. This is solved by the present disclosure by measuring the absolute or differential value of electrode-capacitance, where the form of the disturbance can be calculated and canceled from the signal. This can be suitably done by applying to the circuit a known added signal current with a frequency preferably above the band-width of interest (e.g. sufficiently above to be separable from the biosignal of interest which is to be measured). Modern signal processing technology allows very sharp cut-off thresholds for frequency filters (hi- or low-pass filters); depending on the biosignal of interest, the added signal current can have a frequency of about 50 Hz or higher, but more preferably about 100 Hz or higher, such as about 200 Hz or higher, such as about 400 Hz or higher or 500 Hz higher, or a value even higher than those. Modern signal processing technology also allows a known form signal to be subtracted from the original signal, even if the bandwidth of the two overlaps. This method is practical where the band of interest is wide.

The signal transmits through the circuit across the overall capacitor formed in the circuit (the known capacitance and the body-capacitance) and therefore the absolute value of the body capacitance can be calculated by comparing the applied signal with the measured signal. As the voltage over the capacitor can have a DC component that is unknown, it is not enough to know the capacitance change to calculate the strength of the disturbance, only the form is known. The strength can however be calculated by comparing the capacity signal with the measured signal, using signal processing methods and convolution. With the form and strength of the disturbance known, the signal can then be cleaned up by the use of subtraction of the disturbance from the signal. The total impedance of a capacitor in a circuit can be described by equation (2):

$$Z=1/(j(2 \times PI \times f \times C)) \quad (2)$$

By separating a frequency component which comprises the frequency of the added signal current, which is sufficiently removed from the biosignal of interest to allow for effective separation of the two, the total impedance can be calculated by determining the voltage of said frequency component.

FIG. 1 shows a general setup of two electrodes in the form of conductive belts wrapped around the body of a human subject 1, comprising a thorax belt 34 and abdomen belt 35. The signals are transmitted by thorax lead 36 and abdomen lead 37 to a high input impedance measurement device 38.

Figure 2:
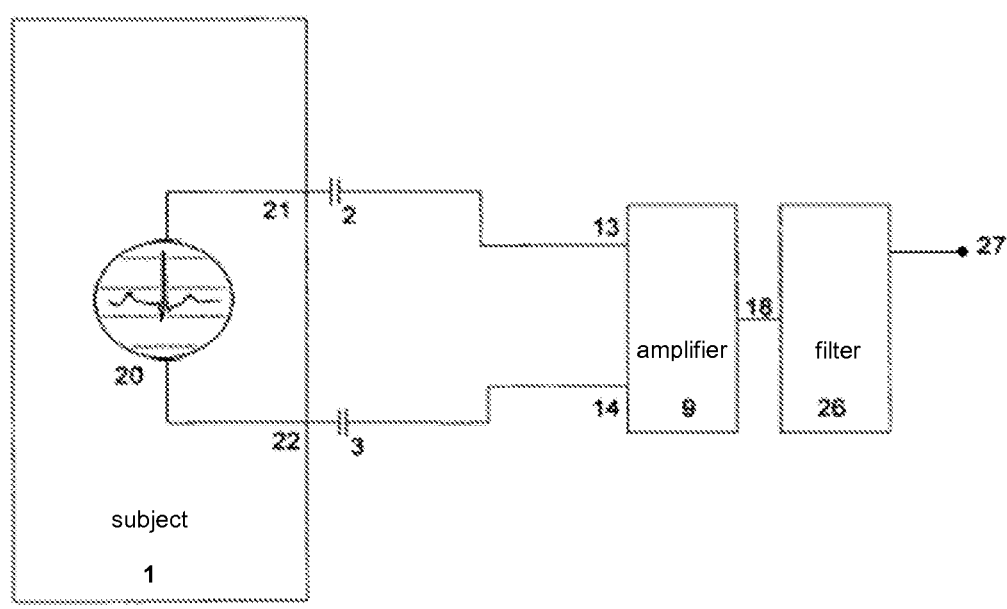
FIG. 2 shows schematically equivalent circuitry of a basic system of another embodiment.

FIG. 2 shows the electrically equivalent circuitry of the system in FIG. 1. The subject 1 generates an electro-physiological signal 20. The thorax belt is positioned at a point/height 21 above the heart but the abdomen belt at a point/height 22 below the heart. The thorax belt forms a capacitor 2 with the body at point 21 and the abdomen belt forms a capacitor 3 with the body at abdomen point 22. The signal picked up is transmitted through the belts and leads to the inputs 13, 14 of a high-input impedance amplifier 9 that delivers a low-impedance signal 18 to further filtering at 26. The signal output 27 is then delivered for further signal processing.

Figure 3:
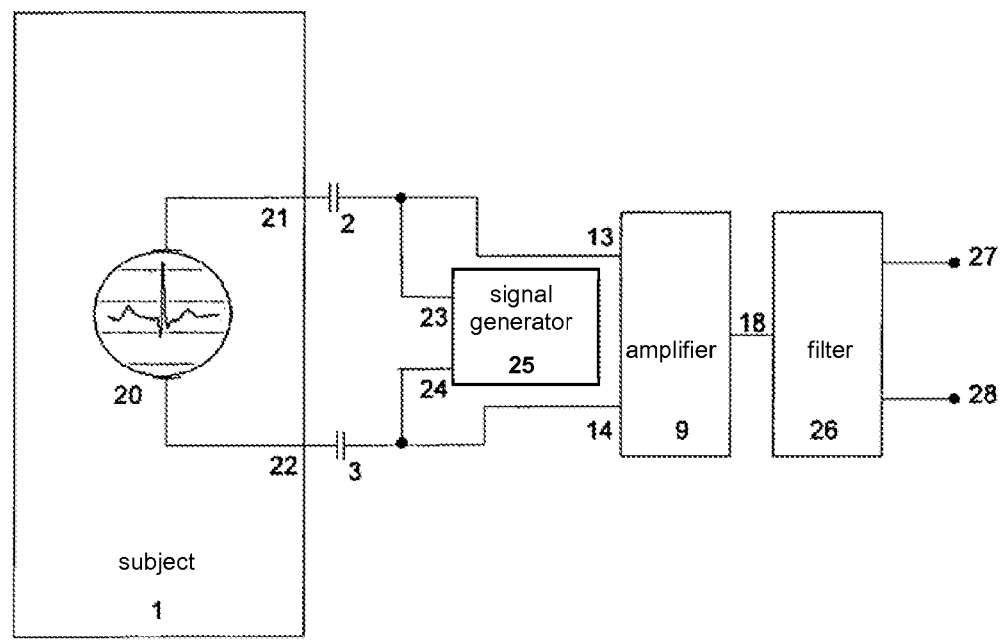
FIG. 3 shows a schematic circuit as in FIG. 2, but with added high-output impedance function generator.

FIG. 3 shows the electrically equivalent circuitry where a signal generator 25 has been added to the circuit of FIG. 2. The high-output impedance function generator 25 generates a differential alternative measurement current between outputs 23 and 24. This current flows through the body 1 over the body-belt capacitors 2 and 3. The frequency of said added current is above the frequency of the biosignal 20 of interest. The signal generated by the current is amplified by the high-input impedance amplifier 9. The output signal of the amplifier 18 contains the sum of both the signal of interest 20 and the signal generated by the generator 25. In this case the signal processing at 26 splits the output signal in two parts, one part 27 containing the signal of interest, and the other part 28 containing information relating to the added signal generated by the generator 25.

Double Use of Respiratory Effort Belts in General

Any conductive belt that is placed on the body forms a capacitor with the body. As long as the impedance between two or more such electrode belts is kept sufficiently high and the body-capacitance is sufficiently high, the electro-physiological voltage signal between the belts can be measured.

Due to the strength of electric signals arising from the heart, ECG measurements are especially suitable for of measurement with the embodiments of the present disclosure. It will be appreciated that in the described embodiments, flexible sensors that have already been placed on the body can include respiratory effort belts.

In a preferred embodiment, the thorax belt is placed around the body at a point 21 above the heart-position, while the abdomen belt is placed at a point 22 below the heart-position. The electronic field caused by the heart, that is the ECG signal, therefore appears between the belts.

In the respiratory effort belts, either the sensors' impedance is modulated with the respiratory movement or the circuit produces an electronic signal internally that is modulated with the respiratory movement. The sensors are therefore configured with two or more leads from each belt. By measuring either the belt impedance or the signal generated by the belt, the respiratory movement is measured.

By measuring the potential between the belts, the ECG can be derived without the use of any conventional electrode and without applying additional sensor. This adds a valuable signal while it keeps the complexity of the setup low and at the level such that measurements can be performed by non-medical personnel.

The double use of the respiratory effort belts is therefore based on measuring the differential or impedance signal for a single belt for the respiratory effort, but to measure the potential signal between two or more belts for the electro-physiological signal.

Figure 4:
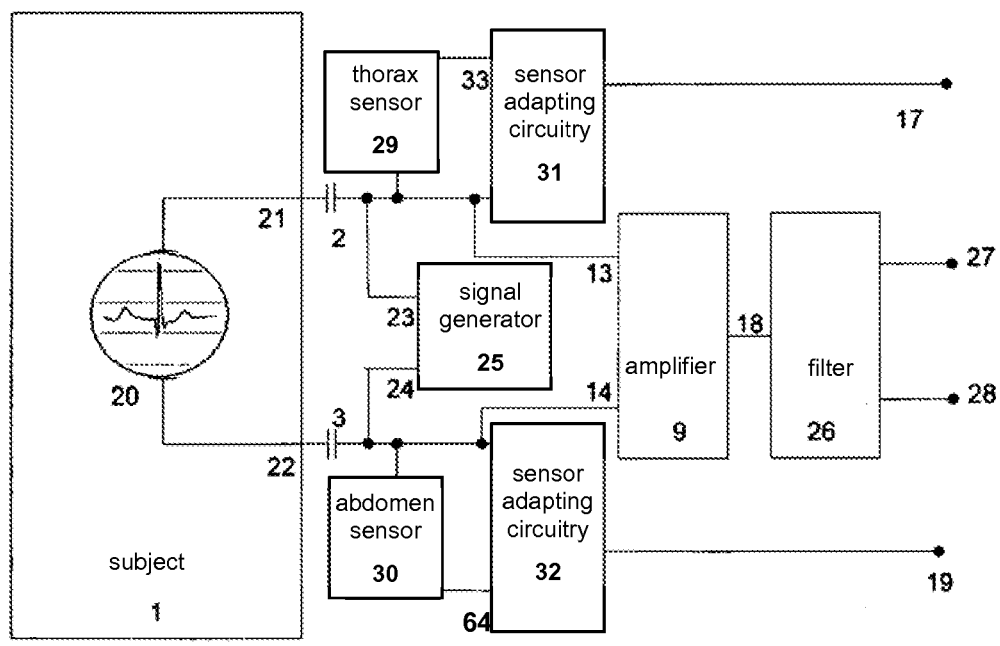
FIG. 4 shows a setup for measuring both ECG, capacitively, and respiratory effort.

FIG. 4 illustrates this setup in more detail. Thorax sensor 29 and abdomen sensor 30 form stray-capacitance 2 and 3 with the body 1 to which the electrodes are applied. The thorax sensor is connected to its sensors adapting circuitry 31 in points 33 and 13. The abdomen sensor is connected to its sensor adapting circuitry 32 in points 64 and 14. The signals generated by the sensors appear on the signal outputs 17 and 19 while the ECG signal appears as before on its signal output 27. As before, this circuit can be used with or without the capacitance measurement unit 25 that delivers additionally information on the capacitance changes and thereby movement artifacts on signal output 28.

Double Use of RIP Belts

The "gold standard" for respiratory belts used in sleep diagnostics are based on the so called RIP technology or Respiratory Inductive Plethysmography. The technology is based on the fact that the inductance of a wire loop is directly proportional to the area of the loop. If a wire is placed tightly around a body of a person, the inductance measured is therefore directly proportional to the cross-sectional area of the body inside the loop, which area changes as the person breathes in and out. By measuring the inductance of one loop around the thorax and one around the abdomen, a good measure of the changes of lung volume can be derived and based on that, the respiratory effort can be calculated.

The wire used to form the inductance does however also form a capacitor with the body. As normally for RIP measurements only the inductance of the belt is measured, the signal is not affected by this capacitance. By measuring the voltage signal between the belts, the ECG can however be derived.

As the capacitance formed between the belts and the body is very low, in the range of hundreds of pF, the isolation between the belts on the device side must be very high. ECG bandwidth is starting around 1 Hz, which requires the input impedance of the device to be above about 1 GOhm. Accordingly, the term "high-input impedance amplifier" as used herein indicates an amplifier with sufficiently high impedance that it becomes substantially larger than the impedance of the capacitor formed in the circuit. Thus, in a high-input impedance amplifier, the impedance should be at least as high as the capacitance of the circuit, and preferably at least 5 times higher and more preferably at least 10 times higher and yet more preferably at least 20 times higher. For measuring ECG signals, which have an inherent voltage of around 10 mV and lie in the frequency spectrum in the range of about 0.5 to 200 Hz, the impedance of suitable capacitive electrodes is in the range of about 1 GOhm or higher, and consequently, a high-input impedance amplifier in such embodiment preferably has an impedance of about 1 GOhm or higher, such as for example 5 GOhm or higher, including 10 GOhm or higher.

Conventional RIP devices do however require a very low output impedance to drive the measurement current for the inductance measurement. Typically this current is in the frequency range of around and above 100 kHz.

Figure 5:
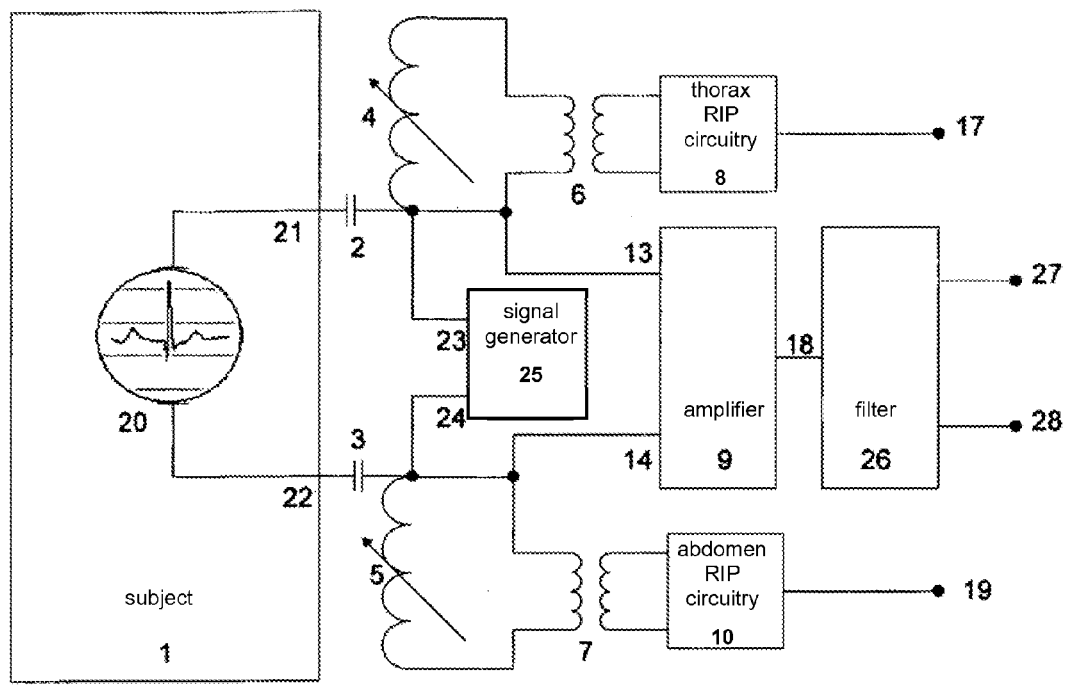
FIG. 5 shows the inductance of a thorax belt and an abdomen belt, being modulated by the respiratory movements of a patient.

In FIG. 5, the inductance of the thorax belt 4 and the abdomen belt 5 are modulated by the respiratory movements of the patient 1. Additionally the wire of the belts forms a stray-capacitance 2 and 3 to the patient. A resonance module is formed for both the thorax 8 and the abdomen 10 RIP belts that deliver signals 17 and 19, containing the respiratory movement signals in one form or the other. The resonance frequency in 8 and 10 is most often measured in tens or hundreds of kHz. A practical problem using the RIP function in combination with capacitive electrode function is that while the electrodes require high input impedance, the impedance of the resonance circuitry is required to be low. To avoid this problem a thorax transformer 6 and abdomen transformers 7 have been added, providing the required high common mode impedance for the electrode but still allowing a low impedance excitation of the RIP belts. As before, this circuit can be used with or without the capacitance measurement unit 25 that delivers additionally information on the capacitance changes and thereby movement artifacts on signal output 28.

Double Use of Piezo Belts

Instead of using RIP belts with a conductor for measuring respiratory effort through inductance measurements, it is also known in the prior art to measure respiratory effort by using elastic belts that pull a piezo-crystal or film at one or more points. The respiratory effort (breathing movements) stretch the elastic belt which this modulates the strain on the piezo material and forms an electronic signal proportional to the movement. If a belt in such application is partially or fully made of conductive materials, they would form a capacitance with the body. Accordingly, in an embodiment of the present disclosure the system comprises one or more piezo-element integrated with one or more elastic belts that comprise electrodes for the primary biosignal measurement, which is suitably an ECG measurement, and the one or more piezo-elements are used for measuring respiratory effort. FIG. 4 illustrates the equivalent electronic circuit for this application, where the sensors 29 and 30 represent piezo elements and the capacitors 2 and 3 are the capacitors formed between the patient 1 and the sensors/conductors within the belts.

Double Use of Resistive Polymer Belts

This type of respiratory effort belts are made from an elastic material that has one or more threads made of elastic polymer that has been blended to give it some conductance. The length and diameter of the polymer threads are modulated with the stretching of the belt, and therefore the belt electrical resistance is also modulated. In this case, either the polymers themselves can be used to form the capacitance with the body, the belt may be coated with conducting material giving the capacitance, or the belt can contain additional conductive materials that form the capacitance. The present disclosure encompasses embodiments with capacitive electrodes for the primary biosignal measurements of the disclosure and where the system comprises resistive polymer sensors for measuring respiratory effort. In this configuration, the resistive polymer sensors need not lie around the patient but can be, e.g., integrated in sheets that when placed appropriately on a subject stretch as the subject breathes.

FIG. 4 describes an equivalent electronic circuit for this application, where the sensors 29 and 30 represent the resistive elements and the capacitors 2 and 3 the capacitors formed between a subject 1 and the sensors/belts. In this case the sensors adapting circuitries 31 and 32 provide the required common mode isolation, to keep the input resistance of the circuitry sufficiently high.

Capacitive electrodes do introduce new sources of disturbances as they are in a weaker connection with the electrical signal than conventional skin electrodes. The high impedance through the capacitance makes them more sensitive for pickup of stray-electro-magnetic fields and as described above, the capacitance is not fixed but is modulated by any movement between the body and the electrode and a modulation of the capacitance is directly coupled into a disturbance artifact directly proportional to the voltage over the capacitor. A method for measuring online the capacitance and using the measured capacitance signal to optimise filtering of those disturbances has already been described above.

Increasing the Body-Electrode Capacitance.

For the flexible electrodes described above, and especially for double use of the respiratory effort belts as capacitive electrodes, the capacitance can be increased and thereby the strength of the measured signal can be increased.

For RIP belts the wire used is normally highly conductive but thin. As the capacitance between the body and the belt is based on the surface area of the conductor across the corresponding area of the body, this capacitance can be suitably increased by increasing this area when using such belts in the present disclosure.

One way of doing this in the present disclosure is to use more than one conductor in parallel in the belt manufacturing and thereby increasing the capacitance area. Two wires in parallel would basically double the belt-body capacitance, etc.

Another way is to give the normally non-conductive RIP-belt base-material some conductance by blending them with conductive material (i.e., mixing in conductive material, soaking in conducting material, or by any other means). The now conductive base material in this way forms capacitance both with the body and with the wire in the RIP belts and thereby increases the overall body-belt capacitance. As the input resistance of the amplifier is very high, the electrical resistance of the belt material does not necessarily need to be very low for this to significantly increase the overall body-belt capacitance.

In another embodiment, the base material is made conductive by having some or all of the belt threads made of conductive materials. This could for example be tinsel-wire, resistive polymer or alike. These conductors would have both capacitive coupling with the RIP-wire and the body and thereby increase the overall body-belt capacitance.

Windowed Pulse Detection.

For many medical applications, it is not necessary to measure all the details of an ECG signal. Often, only the timing of the ECG pulse is of interest and therefore only the R-component of the ECG is of interest in such situations. The R-component is a spike that is significantly larger in amplitude than other components of the ECG signal, so it can be detected from signals with relatively low signal-to-noise ratio (SNR). In the case of recording with capacitive electrodes, it can be the case that the SNR is significantly lower compared with conventional skin-electrodes. The timing of the R-component is of special interest in sleep diagnostics, as it is both used for heart-rate measurements, heart-rate variability measurements and calculations of pulse transit time. If the signal has a low signal-to-noise ratio, the capability of positioning the R-component can be significantly improved by limiting the time-window where it may have appeared. In sleep diagnostics the time-window of the R-component can be limited in two ways.

If a pulse oxymeter signal is recorded simultaneously, every heartbeat results in a pulse in the oxymeter plethysmogram, few milliseconds later. This information can be used to limit the time-window to the last few milliseconds before the oxymeter pulse.

If the movements of the thorax are being monitored using respiratory effort belts, the motoric function of the heart-beat is picked up along with the respiratory signals. As this function is always a result the electrical function few milliseconds before, the position of the motoric pulse can be used to reduce the search area for the electrical pulse.

The present disclosure is however not limited to such embodiments as just mentioned; in other useful embodiments, more heart signals are measured, comprised in normal ECG measurements, such as but not limited to the QRS complex, the P wave, the PR interval, the ST segment, the CT segments, etc. These signals are useful for diagnosing various heart conditions, such as cardiac arrhythmias, conduction abnormalities, ventricular hypertrophy, myocardial infarction, electrolyte derangements, and other disease states.

The Use of Flexible Electrodes for Other Signals than ECG.

In general it is more comfortable to put a belt on rather than to put on a conventional electrode with direct conductive contact with the skin. The belts can therefore also be used instead of electrodes without sharing any function with RIP technology. This may for example be practical to measure EMG signals on limbs using two straps instead of electrode, EMG between neck and thorax used for example for sleep/wake determination or to form a simple-to-put-on EEG/EOG assembly of electrodes, by introducing conductive wire into an elastic cap covering head areas of interest.

The invention claimed is:

1. A system for measuring biometric signals, the system comprising:
a signal processor connected to a first electrode and to a second electrode, the signal processor being configured to process signals output from the first electrode and the second electrode, wherein
the first electrode is a capacitive electrode that includes a flexible conductive structure, and
the signal processor includes a signal isolator, the signal isolator being configured to isolate a low impedance signal and a high impedance signal from the signal output from at least one of the first electrode or the second electrode,
wherein the system is configured to determine a respiratory effort of a subject, based on the low impedance signal, while determining a cardiac indication based on the high impedance signal and a voltage difference between the first electrode and the second electrode.

2. The system of claim 1, wherein the second electrode is a capacitive electrode that includes a flexible conductive structure.

3. The system of claim 2, wherein the first electrode and the second electrode are each elastically deformable.

4. The system of claim 2, wherein the first electrode and the second electrode are each configured to be placed tightly on the body of the subject.

5. The system of claim 2, wherein the first electrode is configured to be placed around a thorax region of the subject, and the second electrode is configured to be placed around an abdomen region of the subject.

6. The system of claim 1, wherein the first electrode and the second electrode each include a pliable belt.

7. The system of claim 6, wherein the pliable belt for each of the first electrode and the second electrode includes an insulated conductor, such that the insulated conductor does not come in galvanic connection with the subject when the belt is placed on said subject.

8. The system of claim 1, wherein the cardiac indication is an electrocardiography (ECG) signal.

9. The system of claim 8, wherein the respiratory effort is determined based on Respiratory Inductive Plethysmography (RIP).

10. The system of claim 9, wherein the signal isolator includes an electronic transformer for a RIP signal that provides high impedance common mode isolation to maintain the capacitive electrode ECG signal level while simultaneously providing low impedance differential mode connection for driving the RIP signal.

11. The system of claim 9, wherein
the first electrode and the second electrode each include a belt, and
each of said belts is configured to form a capacitive strap electrode configured to measure electromyography (EMG) signals.

12. The system of claim 8, wherein
the first electrode or the second electrode includes a pliable belt, and
the system further comprises a piezo element configured to measure the respiratory effort based on a measurement of a stretch of the pliable belt.

13. The system of claim 8, wherein
the first electrode or the second electrode includes a pliable belt made of an elastic material, and
the system further comprising resistive polymer sensors configured to measure the respiratory effort based on a measurement of a stretch of the pliable belt.

14. The system of claim 1, further comprising a correcting unit configured to correct the cardiac indication for fluctuations in a capacitance in a circuit of the signal processor.

15. The system of claim 14, further comprising a signal generator configured to generate and add an added current signal having a known form to the first electrode or the second electrode, and a voltage measurement unit configured to measure a voltage signal that includes a sum of the added current signal and a biosignal indicative of the respiratory effort or the cardiac indication of the subject, and a signal splitter configured to split the voltage signal measured by the voltage measurement unit into a biosignal component and an added signal component.

16. The system of claim 15, wherein said added current signal has a frequency of about 50 Hz or higher.

17. The system of claim 1, wherein the first or the second electrode is included in an elastic covering configured to be placed on the head or limbs of the subject.

18. A method for measuring biosignals from a subject, the method comprising:
placing a first electrode and a second electrode of a system on the subject, each of the first electrode and the second electrode being connected to a signal processor of the system, the signal processor being configured to process signals output from the first electrode and the second electrode;

receiving the signals output from the first electrode and the second electrode;

isolating a low impedance signal from a high impedance signal from the signal output from at least one of the first electrode or the second electrode; and determining a respiratory effort of the subject based on the low impedance signal while determining a cardiac indication based on the high impedance signal and a voltage difference between the first and the second electrode.

19. The method of claim 18, further comprising:

generating and adding an added current signal having a known form to the first electrode or the second electrode, said added current signal having a shape separable from a biosignal indicative of the respiratory effort or the cardiac indication of the subject; and determining fluctuations in overall impedance or fluctuations in capacitance of the system by measuring fluctuations in a measured voltage signal of the added current signal.

* * * * *